United States Patent [19]

Cross

[11] 4,046,797
[45] Sept. 6, 1977

[54] 1-METHOXY-1-METHYL-3-{P-[(1,1-DIMETHYL-2-PROPYNYLOXY)-METHOXY]PHENYL}UREA

[75] Inventor: Barrington Cross, Rocky Hill, N.J.

[73] Assignee: American Cyanamid Company, Stamford, Conn.

[21] Appl. No.: 674,474

[22] Filed: Apr. 7, 1976

Related U.S. Application Data

[62] Division of Ser. No. 584,543, June 6, 1975, which is a division of Ser. No. 283,603, Aug. 24, 1972, abandoned.

[51] Int. Cl.² .................. C07C 127/15; C07C 127/19; A01N 9/20; C07C 83/08
[52] U.S. Cl. .......................... 260/453 R; 260/465 D; 260/553 A; 71/105; 71/120
[58] Field of Search ............ 260/553 A, 453 R; 71/120

[56] References Cited

U.S. PATENT DOCUMENTS

| 3,780,104 | 12/1973 | Teach | 260/553 A X |
|---|---|---|---|
| 3,864,395 | 2/1975 | Martin et al. | 260/553 A |
| 3,885,948 | 5/1975 | Baker et al. | 260/553 A X |
| 3,903,156 | 9/1975 | Teach | 260/553 A |
| 3,937,726 | 2/1976 | Scherer et al. | 260/553 A |
| 3,951,641 | 4/1976 | Janiak | 71/120 |

FOREIGN PATENT DOCUMENTS

| 1,072,982 | 1/1960 | Germany | 260/553 A |
|---|---|---|---|
| 473,534 | 7/1969 | Switzerland | 260/553 A |
| 1,232,748 | 5/1971 | United Kingdom | 260/553 A |
| 999,862 | 7/1965 | United Kingdom | 260/553 A |

*Primary Examiner*—Daniel E. Wyman
*Assistant Examiner*—Thomas A. Waltz
*Attorney, Agent, or Firm*—H. G. Jackson

[57] ABSTRACT

This invention relates to novel (alkenyloxy), (alkynyloxy) and (cyanoalkoxy) alkoxyphenyl ureas and their use as herbicidal agents.

1 Claim, No Drawings

1-METHOXY-1-METHYL-3-{P-[(1,1-DIMETHYL-2-PROPYNYLOXY)-METHOXY]PHENYL}UREA

This is a division, of application Ser. No. 584,543 filed June 6, 1975 which is a division of Ser. No. 283,603, filed Aug. 24, 1972 now abandoned.

BACKGROUND OF THE INVENTION

1. Field of the Invention

The invention pertains to new chemical compounds and their use as herbicides.

2. Description of the Prior Art

Phenylureas have been known for sometime to be herbicidal. Examples are the phenylureas claimed in U.S. Pat. Nos. 2,655,445 (1953) and 2,960,534 (1960).

Additionally, 4-alkyloxymethoxy phenylureas are disclosed in Netherland's Pat. NE No. 69,06047 (basic SW Pat. No. 5829/68).

Although (alkynyloxy)phenyl ureas are known to the art (e.g., to Ciba, Belgian BE No. 756314) alkynyloxyalkoxy and alkenyloxyalkoxy substituted phenylureas are novel. They also offer advantageous selectivity properties and activity compared with the aforementioned art.

SUMMARY OF THE INVENTION

The invention relates to novel (alkenyloxy)alkoxy phenylureas, (alkynyloxy)alkoxy phenylureas and cyanoalkoxyalkoxy phenylureas represented by the formula:

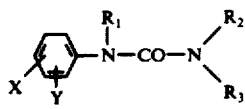

I wherein X is hydrogen, halogen, alkyl $C_1$-$C_4$, alkoxy $C_1$-$C_4$, monohaloalkyl $C_1$-$C_4$, dihaloalkyl $C_1$-$C_4$, trihaloalkyl $C_1$-$C_4$ or nitro; Y is

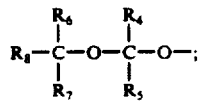

$R_1$, $R_2$ and $R_3$ each represent hydrogen, alkyl $C_1$-$C_4$ or alkoxy $C_1$-$C_4$; $R_4$, $R_5$, $R_6$ and $R_7$ each represent hydrogen or methyl; $R_8$ is —CN,

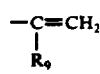

or —C≡C—$R_{10}$; $R_9$ is hydrogen, halogen or methyl; $R_{10}$ is hydrogen, methyl, halogen or halomethyl; with the proviso that the members represented by X and Y are respectively attached to the carbons in the ring which are meta- and para- to the ring carbon attached to the nitrogen or they are respectively para- and meta- to the ring carbon attached to the nitrogen and a process for controlling undesirable vegetation therewith.

DESCRIPTION OF THE PREFERRED EMBODIMENTS

The invention is novel (alkenyloxy)alkoxy phenylureas, (alkynyloxy)alkoxy phenylureas and cyanoalkoxy alkoxyphenylureas defined in detail in the Summary above, and a method for controlling undesirable plant species by applying a herbicidally effective amount of a compound of the above structure to the foliage of the undesirable plants or to soil containing seeds of the undesirable plants.

As used in the specification and claims, the term "halogen" is intended to include fluorine, chlorine, bromine and iodine.

In accordance with this invention, compounds having the structure:

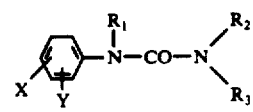

I where X, Y, $R_1$, $R_2$ and $R_3$ are as described above, can be prepared by dissolving a ureido phenol (II) of the structure:

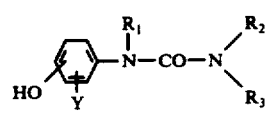

II where $R_1$, $R_2$, $R_3$ and Y are as described, in a lower alcohol, preferably methanol or ethanol, and treating the resulting mixture with an alkali metal. The alkali metal is preferably in the form of an alkali metal alkoxide, alkali metal hydroxide or butyl lithium in ether. Representative alkoxides and hydroxides are sodium methoxide, sodium ethoxide, potassium t-butoxide, sodium hydroxide and potassium hydroxide. The thus-prepared reaction mixture is then gently heated at reflux, i.e. 65° to 78° C., for about 30 minutes and the solvent removed. The product (III) is dried by azeotropic distillation using benzene, toluene or similar solvent and has the formula:

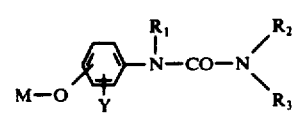

III where X, $R_1$, $R_2$ and $R_3$ are as described above and M represents an alkali metal. The dry product (III) obtained from this reaction is then suspended in a dry loweralkylketone such as acetone, methylethylketone, or the like, maintained at between about 0° and 30° C. and the appropriate cyanoalkyl-, alkenyl- or alkynyl-chloroalkyl ether (IV) slowly added thereto with continuous stirring. The reaction is exothermic and almost instantaneous. However, in practice it is generally desirable to continue stirring the reaction mixture for about 30 minutes to 24 hours after addition is complete.

The reaction mixture is then poured into about four volumes of ice water containing from about 1% to 10% of an alkali metal carbonate or acetate. After stirring for a period of time, usually up to 5 hours, solid product generally forms and can be separated by any convenient means such as filtration or centrifugation. In some cases, however, chloroform extraction, evaporation and crystallization of the residue may be required. An advantageous variation of this process involves the preparation of the salt III in a solvent in which it remains in solution so that the addition of the appropriate chloroalkyl ether may be made to the solution e.g., DMF is a useful solvent for a homogeneous reaction. Work up by pouring into water as previously described is the method of isolating the product as a precipitate. The reaction can be graphically illustrated as follows:

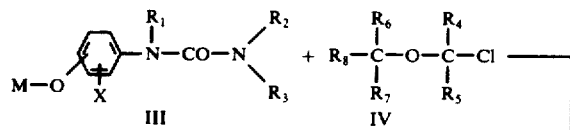

where $R_1$-$R_8$, X and M are as defined above.

Alternatively the phenylureas of the present invention may be prepared from substituted nitrophenols (V). The reaction involves treating the substituted nitrophenol (V) with an alkali metal hydroxide or alkoxide in the presence of a lower alcohol $C_1$-$C_4$ to form the corresponding alkoxide (VI). This product is then treated with the alkenyl or alkynylchloroalkyl ether to form the alkenyloxy or (alkynyloxy)alkoxynitrobenzene (VII) which can be selectively reduced by reaction with lithium aluminum hydride in a solvent, e.g. an ether such as diethyl ether or tetrahydrofuran. The alkenyloxy- or (alkynyloxy)alkoxyaniline (VIII) can then be treated with the appropriate carbamoyl halide, preferably chloride, to yield the desired alkenyloxy- or (alkynyloxy)alkoxyphenylurea.

In yet another procedure the aniline from above may be treated with phosgene to give a mixture of the isocyanate and carbamoyl chloride. This mixture is then treated with the appropriate amine or alkylamine to yield the desired alkenyloxy- or (alkynyloxy)alkoxyphenylurea (I). The above reactions are graphically illustrated below:

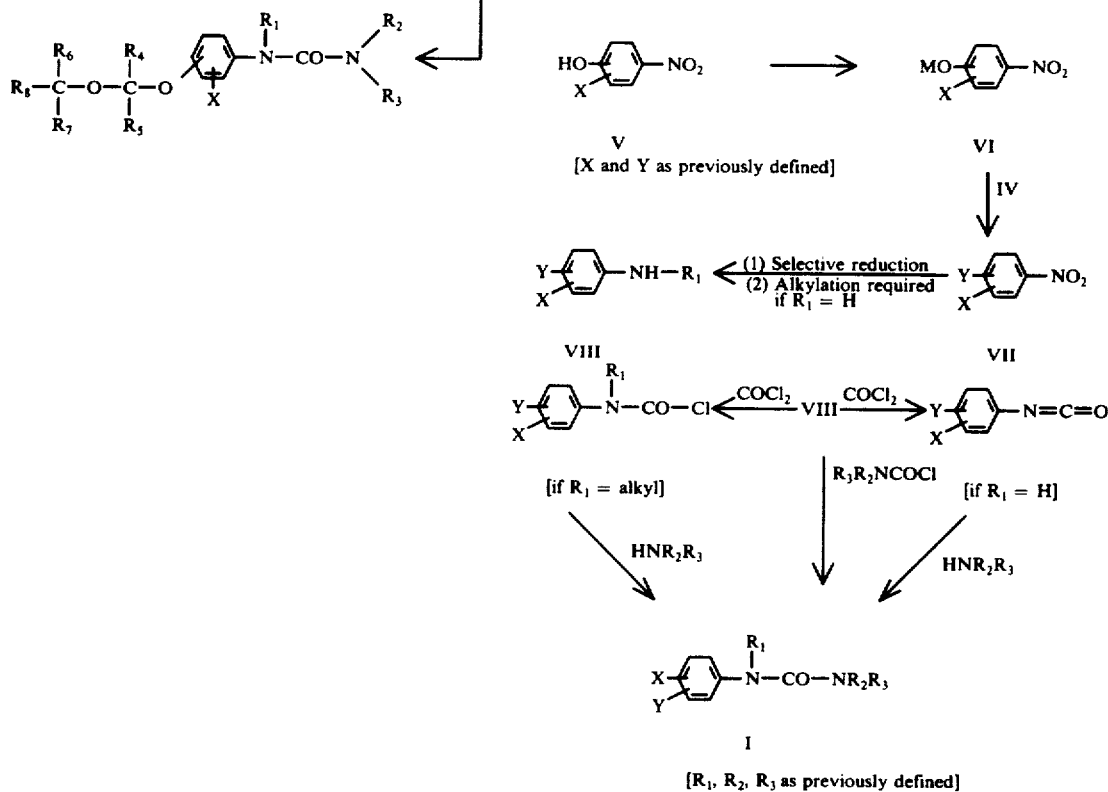

The ureido phenols employed as starting materials in the preferred synthesis route can be prepared by the phosgenation of the appropriately substituted meta- or para- aminophenol in an aprotic solvent to yield the intermediate isocyanate. The isocyanate is then reacted with the appropriate primary or secondary amine to yield the ureido phenol.

Alternatively, the ureido phenols can be prepared by carbamoylation of the aminophenol in an aprotic solvent using a dialkylcarbamoyl chloride or alkylalkoxycarbamoyl chloride in the presence of a base acceptor such as sodium bicarbonate or pyridine.

Among the ureido phenols prepared by the above procedure and useful in the synthesis of the compounds of this invention are:

| COMPOUND | MELTING POINT |
|---|---|
| 1,1-Dimethyl-3-(3-chloro-4-hydroxyphenyl)urea | 211–212° C. |
| 1,1-Dimethyl-3-(4-hydroxyphenyl)urea | 208–210° C. |
| 1,1-Dimethyl-3-(3-hydroxyphenyl)urea | 195–197° C. |
| 1-(3-Chloro-4-hydroxyphenyl)-3-methylurea | 188–189° C. |
| 1-(4-Hydroxyphenyl)-3-methylurea | 164–165° C. |
| 1-(3-Hydroxyphenyl)-3-methylurea | 139–140° C. |

| COMPOUND | MELTING POINT |
| --- | --- |
| 3-(4-Hydroxyphenyl)-1-methoxy-1-methylurea | 143-145° C. |
| 3-(3-Chloro-4-hydroxyphenyl)-1-methoxy-1-methylurea | 133-134° C. |
| 1,1-Dimethyl-3(4-hydroxy-3-nitropheyl)urea | 134-138° C. |
| 1-(4-Hydroxy-3-nitrophenyl)-3-methylurea | 195-197° C. |
| 1-Ethyl-3-(3-chloro-4-hydroxyphenyl)urea | 156-158° C. |
| 1-(3-Chloro-4-hydroxyphenyl)-3-n-propylurea | 169-170° C. |
| 1-(3-Chloro-4-hydroxyphenyl)-3-iso-propylurea | 180.5-181.5° C. |
| 1-n-Butyl-3-(3-chloro-4-hydroxyphenyl)urea | 145-148° C. |
| 1-(3-Chloro-4-hydroxyphenyl)-3,3-diethylurea | 136-137° C. |

The chloroalkylakynyl (or alkenyl) ethers utilized as intermediates in the preferred procedure for the preparation of the compounds of this invention can be prepared by reacting the appropriate alkynyl or alkenyl alcohol with an aldehyde such as para- formaldehyde and hydrogen chloride at −30° C. to +20° C. in the absence or presence of a solvent (e.g. methylene chloride). Among the compounds prepared by this procedure are: chloromethyl 2-propynyl ether, boiling point 38° to 43° C./34 to 36 mm.; chloromethyl 1-methyl-2-propynyl ether, boiling point 36° to 39° C./32 mm.; chloromethyl 1,1-dimethyl-2-propynyl ether, boiling point 39.5° C. to 41.5° C./16 to 17 mm.; 2-methylallyl chloromethyl ether, boiling point 60° to 63° C./44 mm.; allyl chloromethyl ether, boiling point 38° to 46° C./70 mm.; 1-chloroethyl 1,1-dimethyl-2-propynyl ether, boiling point 57° to 58° C./55 mm.; 1-chloroethyl 1-methyl-2-propynyl ether, boiling point 68° to 70° C./111 to 115 mm.; and 1-chloroethyl 2-propynyl ether, boiling point 57° to 63° C./57 to 60 mm.

The compounds of this invention, especially those having the structure:

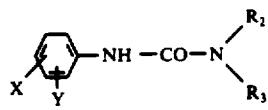

where $R_2$, $R_3$, X and Y are as described above, are highly effective herbicidal agents. They provide selective control of a wide variety of broadleaf weeds and grasses and may be used for either preemergence or postemergence control of undesirable plants. They may be used alone or in combination with other herbicides and are particularly effective when utilized for the control of undesirable weeds and grasses in the presence of agronomic crops such as corn, cotton, soybeans and rice.

The active compounds can be incorporated in liquid or solid formulations and applied as such to the foliage of undesirable plants or to soil containing seeds of undesirable plants.

Among the solid formulations which can be prepared are dusts, dust concentrates, wettable powders and granular formulations.

Dusts are usually prepared by dissolving the active ingredient in a lower alcohol (e.g. methanol, isopropanol or butanol) or a ketone (e.g. acetone, methylethylketone or cyclohexanone) and spraying the thus-prepared solution on a finely divided carrier such as attapulgite, kaolin, diatomaceous earth, or the like. Dusts usually contain about 1% to 15% by weight of the active compound.

Dust concentrates are generally prepared in the same fashion as dusts excepting that about 16% to about 75% by weight of the active compound is applied to the carrier.

Wettable powders are made up in the same manner as the dust concentrates; however, about 1% to 10% by weight of a surfactant is usually added. In some instances, about 1% to 5% by weight of a dispersant and about 1% to 5% of an anionic —nonionic emulsifier is used in place of a single surfactant. In practice, the wettable powders are generally dispersed in water or other suitable liquid and applied to the soil or foliage as a dilute spray.

Surfactants which may be used in preparation of the wettable powders are naphthalene sulfonic acid condensate, polyoxyethylate vegetable oil, Sorbitan monooleate, mono- and diglycerides of fatty acids, alkyl phenoxy polyoxyethylene ethanol and sodium alkylnaphthalene sulfonate. The mono-calcium salt of a polymerized alkyl aryl sulfonic acid and sodium lignin sulfonate are representative of dispersants which can be used in the wettable powder formulations. Also, MAL-77L, an anionic-nonionic blend containing calcium dodecylbenzene sulfonate, is representative of the emulsifiers which may be used in the wettable powders.

Granular formulations can be prepared by applying an alcoholic or ketonic solution of the active material to a granular sorptive carrier such as attapulgite, kaolin, activated carbon or corn cob grits. Non-sorptive carriers such as granular limestone, walnut shell, cocoanut shell or sand may be used in the preparation of granular formulations by (1) wetting the granules with a binder solution (e.g., sodium lignosulfonate) or an alcoholic or ketonic solution of the active ingredient, and (2) coating the wetted particles with a dust or dust concentrate containing the active compound or with an inert dusting agent such as talc or clay.

Emulsifiable concentrates can be prepared by dissolving above 25% to 75% by weight of the active compound in a lower alcohol or ketone, as mentioned above, and admixing therewith from about 1% to 10% by weight of an emulsifier. For use in the field, the concentrate is usually dispersed in water or other suitable diluent and applied as a liquid spray.

Effective control of a wide variety of broadleaf weeds and grasses is usually obtained by application of a sufficient amount of the formulated composition to provide about 0.06 pounds per acre to 15 pounds per acre of active compound. Selective control of said weeds and grasses, on the other hand, generally requires only about 0.06 pounds per acre to about 4.0 pounds per acre of the active compound.

This invention is further illustrated by the following examples.

EXAMPLES 1 through 32

3-{3-Chloro-4-[(1,1-dimethyl-2-propynyloxy)methoxy]phenyl} urea

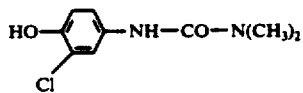

(1) NaOMe
(2) Cl—CH₂—OC(CH₃)₂C≡CH

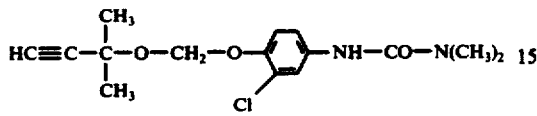

Sodium methoxide (0.54 gram, 0.01 mole) is added to a methanolic solution of 3-(3-chloro-4-hydroxyphenyl)-1,1-dimethylurea (2.14 grams, 0.01 mole) and the mixture heated at reflux during 2 hours. The solvent is removed under reduced pressure and to the residual material dry benzene is added and evaporated off. This procedure is repeated until a dry white powder is obtained. The sodium salt is suspended in dry acetone (50 ml.) and chloromethyl 1,1-dimethyl-2-propynyl ether (1.45 grams, 0.011 mole) is added dropwise with stirring. After the initial exothermic reaction the reaction mixture is allowed to stir for a further 4.5 hours, then cold aqueous sodium carbonate solution (10% w/v, 100 ml.) followed by water (50 ml.) are added[1] and stirred. The resulting solid[2] is filtered off, water washed and air dried. Crystallization from benzene-hexane affords 2.2 grams, 70%; melting point 150° to 151° C. of Compound 1.

[1] In some examples in Table I, the reaction mixture is poured into aqueous sodium carbonate solution (rather than as above).
[2] Chloroform extraction followed by evaporation and crystallization of the residue was alternatively used as a route to the product.

The following compounds (Compounds 1 through 32) are prepared according to the above procedures using the appropriate ureido phenol (II). Among the ureido phenols that may be used in this process are those listed above.

TABLE I

| Compound Number | Starting Chloromethyl Ether | Compound Prepared | Solvent of Crystallization | Melting Point °C. | Analysis % Calculated | Analysis % Found |
|---|---|---|---|---|---|---|
| 1 | Cl—CH₂—O—C(CH₃)₂—C≡CH | 3-{3-chloro-4-[(1,1-dimethyl-2-propynyloxy)methoxy]phenyl}-1,1-dimethylurea | benzene-hexane | 150–151 | C, 58.0  H, 6.2  N, 9.0  Cl, 11.4 | C, 58.7  H, 6.3  N, 8.8  Cl, 11.4 |
| 2 | Cl—CH₂—O—CH₂—C≡CH | 1,1-dimethyl-3-{p-[(2-propynyloxy)methoxy]phenyl}urea | benzene-hexane | 113.5–114.5 | C, 62.9  H, 6.5  N, 11.3 | C, 62.8  H, 6.5  N, 11.2 |
| 3 | Cl—CH₂—O—C(CH₃)₂—C≡CH | 3-{p-[(1,1-dimethyl-2-propynyloxy)methoxy]phenyl}-1,1-dimethylurea | benzene-hexane | 75–76 | C, 65.2  H, 7.3  N, 10.1 | C, 65.4  H, 7.2  N, 10.1 |
| 4 | Cl—CH₂—O—CH₂—C≡CH | 3-{3-chloro-4-[(2-propynyloxy)methoxy]phenyl}-1,1-dimethylurea | benzene-hexane | 114–115 | C, 55.2  H, 5.4  N, 9.9  Cl, 12.5 | C, 55.8  H, 5.4  N, 9.9  Cl, 12.5 |
| 5 | Cl—CH₂—O—CH—C≡CH  (CH₃) | 3-{3-chloro-4-[(1-methyl-2-propynyloxy)methoxy]phenyl}-1,1-dimethylurea | benzene-hexane | 106–107 | C, 56.7  H, 5.8  N, 9.4  Cl, 12.0 | C, 56.8  H, 5.9  N, 9.6  Cl, 11.4 |
| 6 | Cl—CH₂—OCH₂—C≡CH | 1,1-dimethyl-3-{m-[(2-propynyloxy)methoxy]phenyl}urea | benzene-hexane | 98–98.5 | C, 62.9  H, 6.5  N, 11.3 | C, 63.0  H, 6.6  N, 11.3 |
| 7 | Cl—CH₂—O—CH—C≡CH  (CH₃) | 3-{m-[(2-propynyloxy)-1-methoxy)-1-methyl]phenyl}urea | — | oil (n_D²⁵ 1.5420) | C, 59.1  H, 6.1  N, 10.6 | C, 58.8  H, 6.1  N, 10.3 |
| 8 | Cl—CH₂—O—CH—C≡CH  (CH₃) | 3-{m-[(1-methyl-2-propynyloxy)methoxy]phenyl}urea | — | oil (n_D²⁵ 1.5322) | C, 60.4  H, 6.5  N, 10.1 | C, 60.5  H, 6.6  N, 10.1 |
| 9 | Cl—CH₂—O—C(CH₃)₂—C≡CH | 3-{m-[(1,1-dimethyl-2-propynyloxy)methoxy]phenyl}-1-methylurea | — | oil (n_D²⁵ 1.5281) | C, 61.6  H, 6.9  N, 9.6 | C, 62.2  H, 6.9  N, 9.2 |
| 10 | Cl—CH₂—OCH₂CH=CH₂ | 3-{4-[(allyloxy)methoxy]-3-chlorophenyl}-1,1-dimethylurea | benzene-hexane | 95–95.5 | C, 54.8  H, 6.0  N, 9.8 | C, 55.2  H, 5.9  N, 9.6 |
| 11 | Cl—CH₂—OCH₂—C≡CH | 3-{m-[(allyloxy)methoxy]phenyl}-1-methoxy-1-methylurea | — | oil (n_D²⁴ 1.5374) | C, 58.6  H, 6.8  N, 10.5 | C, 58.3  H, 6.8  N, 10.6 |
| 12 | Cl—CH₂—OCH₂—C≡CH | 3-{3-chloro-4-[(2-propynyloxy)methoxy]phenyl}-1-methoxy-1-methylurea | benzene-hexane | 143–145 | C, 53.6  H, 4.9  N, 10.5 | C, 54.5  H, 4.8  N, 10.6 |
| 13 | Cl—CH₂—O—C(CH₃)₂—C≡CH | 3-{p-[(1,1-dimethyl-2-propynyloxy)methoxy]phenyl}-1,3-dimethylurea | benzene-hexane | 127–128 | C, 56.7  H, 5.8  N, 9.4 | C, 57.0  H, 5.9  N, 9.5 |
| 14 | Cl—CH₂—OCH₂—C≡CH | 3-{3-chloro-4-[(2-propynyloxy)methoxy]phenyl}-1-methylurea | benzene-hexane | 81.5–83 | C, 52.3  H, 5.1  N, 9.3 | C, 52.0  H, 5.1  N, 9.2 |

TABLE I-continued

| Compound Number | Starting Chloromethyl Ether | Compound Prepared | Solvent of Crystallization | Melting Point °C. | Analysis Calculated % | Analysis Found % |
|---|---|---|---|---|---|---|
| 15 | Cl—CH₂—O—CH₂—C≡CH | 3-{3-chloro-4-[(1,1-dimethyl-2-propynyloxy)methoxy]phenyl}-1-methoxy-1-methylurea | benzene-hexane | 96-97 | C, 55.1; H, 5.9; N, 8.6 | C, 56.0; H, 6.0; N, 8.4 |
| 16 | Cl—CH₂—O—CH₂—C≡CH | 1,1-dimethyl-3-{p-[(2-methylallyloxy)methoxy]phenyl}urea | benzene-hexane | 99-100 | C, 63.6; H, 7.6; N, 10.6 | C, 63.0; H, 7.9; N, 10.0 |
| 17 | Cl—CH₂—O—CH₂—CH=CH₂ CH₃ | 1,1-dimethyl-3-{m-[(1,1-dimethyl-2-propynyloxy)methoxy]phenyl}urea | benzene-hexane | 104-105 | C, 65.19; H, 7.30; N, 10.14 | C, 65.7; H, 7.2; N, 10.0 |
| 18 | Cl—CH₂—O—C—C≡CH CH₃ | 1-{p-[(1,1-dimethyl-2-propynyloxy)methoxy]phenyl}-3-methylurea | benzene | 150-151 | C, 64.1; H, 6.9; N, 10.7 | C, 64.2; H, 6.9; N, 10.4 |
| 19 | Cl—CH₂—O—CH₂—C≡CH | 1-methyl-3-{p-[(2-propynyloxy)methoxy]phenyl}urea | benzene-hexane | 149-150.3 | C, 61.5; H, 6.0; N, 12.0 | C, 61.6; H, 6.0; N, 11.8 |
| 20 | Cl—CH₂—O—C—C≡CH CH₃ | 1-methoxy-1-methyl-3-{p-[(1,1-dimethyl-2-propynyloxy)methoxy]phenyl}urea | benzene-hexane | 70-71 | C, 61.6; H, 6.9; N, 9.6 | C, 61.4; H, 6.8; N, 9.4 |
| 21 | Cl—CH₂—O—CH₂—C≡CH | 1-methoxy-1-methyl-3-{p-[(2-propynyloxy)methoxy]phenyl}urea | hexane | 85-86 | C, 59.1; H, 6.1; N, 10.6 | C, 59.0; H, 6.1; N, 10.6 |
| 22 | Cl—CH₂—O—C—C≡CH CH₃ | 3-{p-[(1,1-dimethyl-2-propynyloxy)ethoxy]phenyl}-1,1-dimethylurea | hexane-benzene (10:1) | 91-93 | C, 66.2; H, 7.6; N, 9.7 | C, 66.3; H, 7.8; N, 9.5 |
| 23 | Cl—CH₂—O—CH—C≡CH CH₃ | 3-{p-[1-(1-methyl-2-propynyloxy)ethoxy]phenyl}-1,1-dimethylurea | benzene-hexane | 111.5-113.5 | C, 65.2; H, 7.3; N, 10.1 | C, 65.2; H, 7.4; N, 10.0 |
| 24 | Cl—CH—O—CH—C≡CH CH₃ CH₃ | 3-{3-chloro-4-[1-(1-methyl-2-propynyloxy)ethoxy]phenyl}-1,1-dimethylurea | hexane | 50-53 | C, 58.0; H, 6.1; N, 9.0 | C, 58.2; H, 6.3; N, 9.3 |
| 25 | Cl—CH—O—CH—C≡CH CH₃ CH₃ | 3-{p-[1-(ω-propynyloxy)ethoxy]phenyl}-1,1-dimethylurea | — | glassy solid | C, 64.1; H, 9.0; N, 6.9 | C, 64.6; H, 7.3; N, 9.3 |
| 26 | Cl—CH—O—CH—C≡CH CH₃ CH₃ | 3-{3-chloro-4-[1-(2-propynyloxy)ethoxy]phenyl}-1,1-dimethylurea | hexane | 93-95 | C, 56.7; H, 5.8; N, 10.7 | C, 58.2; H, 6.3; N, 10.4 |
| 27 | Cl—CH₂—OCH₂—C≡CH | 3-{[3-chloro-4-(2-propynyloxy)methoxy]phenyl}-1-ethylurea | benzene-hexane | 141.5-143 | C, 55.2; H, 5.4; N, 9.4 | C, 54.9; H, 5.2; N, 9.3 |
| 28 | Cl—CH₂—OCH₂—C≡CH | 1-n-propyl-3-{[3-chloro-4-(2-propynyloxy)methoxy]phenyl}urea | benzene-hexane | 123-124 | C, 56.7; H, 5.8; N, 9.9 | C, 56.6; H, 5.7; N, 9.6 |
| 29 | Cl—CH₂—OCH₂—C≡CH | 1-iso-propyl-3-{[3-chloro-4-(2-propynyloxy)methoxy]phenyl}urea | benzene-hexane | 122-123 | C, 56.7; H, 5.8; N, 9.4 | C, 56.5; H, 5.8; N, 9.3 |

TABLE I-continued

| Compound Number | Starting Chloromethyl Ether | Compound Prepared | Solvent of Crystallization | Melting Point °C. | Analysis % Calculated | Analysis % Found |
|---|---|---|---|---|---|---|
| 30 | Cl—CH$_2$—OCH$_2$—C≡CH | 1-n-butyl-3-(e-chloro-4-(2-propynyloxy)methoxy)phenyl) urea | benzene-hexane | 112-113 | N, 9.4 C, 58.0 H, 6.2 | H, 9.1 C, 58.1 H, 6.1 |
| 31 | Cl—CH$_2$—O—CH—C≡CH<br>             CH$_3$ | 1-(3-chloro-4-[(1-methyl)-2-propynyloxy)methoxy)phenyl)-3-methyl | ethylacetate-benzene-hexane | 153-154 | N, 9.0 C, 55.2 H, 5.4 N, 9.9 | N, 8.9 C, 55.3 H, 5.4 N, 9.8 |
| 32 | Cl—CH—O—C—C≡CH<br>   CH$_3$  CH$_3$<br>          CH$_3$ | 3-(3-chloro-4-[1-(1,1-dimethyl-2-propynyloxy)ethoxy]-phenyl)-1,1-dimethylurea | benzene-hexane | 101-103 | C, 59.17 H, 6.52 N, 8.62 | C, 59.17 H, 6.5 N, 8.66 |

EXAMPLE 33

Preparation of
3-{3-Chloro-4-[1-(1,1-dimethyl-2-propynyloxy)-ethoxy]phenyl}-1,1-dimethylurea

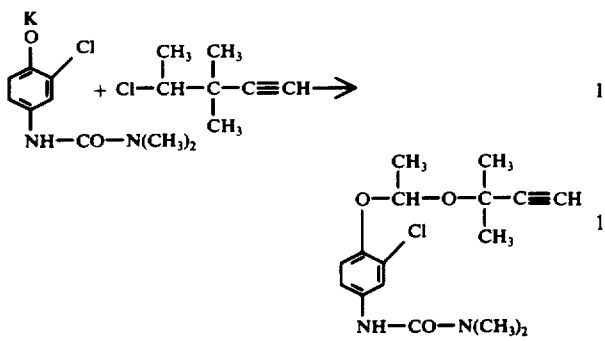

To a well-stirred suspension of the potassium salt of 3-chloro-4-hydroxyphenyl-1,1-dimethylurea (0.04 mole) in dry acetone (150 ml.) is added dropwise 1-chloroethyl 1,1-dimethyl-2-propynyl ether (5.9 grams, 0.04 mole). During the addition, an exotherm to 35° C. is observed; the reaction is stirred at room temperature overnight, then poured into an aqueous 10% sodium carbonate solution containing 200 grams of ice, and the mixture stirred vigorously for 30 minutes. The resulting solid is filtered off, water-washed and dried to give 8.5 grams, melting point 99° to 101° C., crystallization from hexane-cyclohexane-benzene gave 4.69 grams (36%), melting point 101° to 103° C.

Analysis Calculated for $C_{16}H_{21}N_2O_3Cl$: C, 59.17; H, 6.52; N, 8.62. Found: C, 59.17; H, 6.56; N, 8.66.

EXAMPLE 34

Preparation of 1-Methyl-2-propynylchloromethyl Ether

Hydrogen chloride gas was bubbled into a suspension of paraformaldehyde (30.1 grams, 1 mole) in 3-butyn-2-ol (70.1 grams, 1 mole), with constant stirring, at −30° C. The exotherm was controlled between −15° C. and 5° C., and the hydrogen chloride addition continued until the solid dissolved. Upon completion of the addition, the reaction was allowed to attain 15° C. and sodium chloride added to aid the separation of the organic layer. The upper organic layer was separated and dried over anhydrous calcium chloride for 3 hours and distilled under reduced pressure to give 1-methyl-2-propynylchloromethyl ether, 83 grams, 70%, boiling point 36° to 39° C./32 mm.

EXAMPLE 35

Preparation of 1,1-Dimethyl-2-propynylchloromethyl Ether

Hydrogen chloride gas (80 grams, 2.2 moles) was bubbled into a mixture of paraformaldehyde (60.2 grams, 2.0 moles), and 2-methyl-3-butyn-2-ol (168.2 grams, 2.0 mole) in methylene chloride (500 ml.) over a 25 minute period, with constant stirring while maintaining the temperature between 2° to 8° C. Upon completion of the addition, the reaction temperature was allowed to rise to 10° C., then the lower organic phase separated, washed with ice water, separated and dried over anhydrous calcium chloride for 18 hours. The methylene chloride was removed by evaporation and the resulting liquid distilled at reduced pressure to give the chloromethyl ether, 1,1-dimethyl-2-propynylchloromethyl ether, 140 grams, 53%, boiling point 54° E. to 58° C./37 to 40 mm.

EXAMPLES 36 through 46

Following the procedure of Example 1 and substituting therein the appropriate ureido phenol and alkynyl chloromethyl ether yields the following compounds:

| Example Number | Structure |
|---|---|
| 36 | $CH\equiv C-CH_2-O-C(CH_3)_2-O-\langle\text{phenyl}\rangle-NH-CON(CH_3)_2$ <br> 1,1-dimethyl-3-{p-[2-propynyloxy)-α,α-dimethylmethoxy]phenyl}urea |
| 37 | $I-C\equiv C-CH_2-O-CH_2-O-\langle\text{phenyl}\rangle-NH-CO-N(CH_3)_2$ <br> 1,1-dimethyl-3-{p[(3-iodo-2-propynyloxy)-methoxy]phenyl}urea |
| 38 | $HC\equiv C-\overset{H}{\underset{CH_3}{C}}-O-CH_2-O-\langle\text{phenyl, Br}\rangle-NH-CO-N(CH_3)_2$ <br> 3-{3-bromo-[1,1-dimethyl-4-propynyloxy)-methoxy]phenyl}-1,1-dimethylurea |
| 39 | $HC\equiv C-CH_2-O-CH_2-O-\langle\text{phenyl, CH}_3\rangle-NH-CO-N(CH_3)_2$ <br> 3-{[3-methyl-4-(2-propynyloxy)methoxy]-phenyl}-urea |
| 40 | $HC\equiv C-CH_2-O-CH_2-O-\langle\text{phenyl, CF}_3\rangle-NH-CO-N(CH_3)_2$ <br> 1,1-dimethyl-3-{[3-trifluoromethyl-4-(2-propynyloxy)methoxy]phenyl}urea |

-continued

| Example Number | Structure |
|---|---|
| 41 | HC≡C—CH$_2$—O—CH$_2$—⟨phenyl, OCH$_3$⟩—NHCO—N(CH$_3$)$_2$<br>1,1-dimethyl-3-{[3-methoxy-4-(2-propynyloxy)-methoxy]phenyl}urea |
| 42 | CH≡C—CH$_2$—O—CH$_2$—O—⟨phenyl, NO$_2$⟩—NH—CO—N(CH$_3$)$_2$<br>1,1-dimethyl-3-}[4-(2-propynyloxy)methoxy-3-nitro]phenyl}urea |
| 43 | Cl—CH$_2$—C≡C—CH$_2$—O—CH$_2$—O—⟨phenyl⟩—NH—CO—N(CH$_3$)$_2$<br>1,1-dimethyl-3-{[4-(4-chloro-2-butynyloxy)-methoxy]phenyl}urea |
| 44 | CH$_3$—C≡C—CH$_2$—O—CH$_2$—O—⟨phenyl⟩—NH—CO—N(CH$_3$)$_2$<br>1,1-dimethyl-3-{[4-(2-butynyloxy)methoxy]-phenyl}urea |
| 45 | N≡C—CH$_2$—O—CH$_2$—O—⟨phenyl⟩—NH—CO—N(CH$_3$)$_2$<br>1,1-dimethyl-3-{[4-(cyanomethoxy)methoxy]-phenyl}urea |
| 46 | N≡C—C(CH$_3$)(CH$_3$)—O—CH$_2$—O—⟨phenyl⟩—NH—CO—N(CH$_3$)$_2$<br>1,1-dimethyl-3-{[4-(1,1-dimethylcyanomethoxy)-methoxy]phenyl}urea |

EXAMPLE 47

The selective postemergence herbicidal acitivity of the preferred compounds of the present invention is demonstrated by the following tests, wherein a variety of monocotyledonous and dicotyledonous plants are treated with test compounds dispersed in aqueous acetone mixtures. In the tests, seedling plates are grown in two-inch square plastic pots for about two weeks. The test compounds are dispersed in 50/50 acetone/water mixtures containing 0.5% v/v surfactant in sufficient quantity to provide the equivalent of about 0.06 to 10 pounds per acre of active compound when applied to the plants through a spray nozzle operating at 40 psi. for a predetermined time. After spraying, the plants are planted on greenhouse benches and are cared for in the usual manner, commensurate with conventional greenhouse practices. Two weeks after treatment, the seedling plants are examined and rated according to the rating system provided below. The data obtained are reported in the Table below where it can be seen that the preferred compounds are highly effective for the control of undesirable broadleaf weeds and grasses in the presence of the desirable crops, rice, corn, cotton and soybeans.

Plant Abbreviations:

- LA - Lambsquarters
- MU - Mustard
- PI - Pigweed
- BA - Barnyardgrass
- CR - Crabgrass
- GRF - Green foxtail
- WO - Wild oats
- COR - Corn
- COT - Cotton
- SOY - Soybean
- RAG - Ragweed
- MG - Morningglory
- R - Rice
- VE - Velvetleaf

| Rating System: | % Difference in Growth From the Check* |
|---|---|
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |

4 - abnormal growth, i.e. a definite physiological mal-formulation but with an over-all effect less than a 5 on the rating scale.

*Based on visual determination of stand, size, vigor, chlorosis, growth malformation and over-all plant appearance.

TABLE II

Postemergence Herbicidal Activity

| Compound of Example Number | Structure | Treatment lb./acre | LA | MU | PI | RAG | MG | VE | BA | CR | GRF | WO | COR | COT | SOY | R |
|---|---|---|---|---|---|---|---|---|---|---|---|---|---|---|---|---|
| 6 | 3-[(HC≡C—CH₂—O—CH₂—O—)phenyl]-NHCON(CH₃)₂ | 1.0 | 9 | 9 | 9 | 9 | — | — | — | — | — | — | 6 | 7 | — | 3 |
|  |  | 0.5 | 9 | 7 | 9 | 9 | — | — | — | — | — | — | 3 | 3 | 9 | 0 |
|  |  | 0.25 | 9 | 9 | 9 | 9 | 2 | 0 | 3 | 0 | 2 | 0 | 2 | 2 | 9 | 1 |
|  |  | 0.13 | 9 | 9 | 9 | 9 | — | — | — | — | — | — | 0 | 0 | — | 0 |
| 2 | HC≡C—CH₂—O—CH₂—O—C₆H₄—NH—CO—N(CH₃)₂ | 1.0 | 9 | 9 | 9 | 9 | 9 | 8 | 3 | 3 | 3 | 3 | 3 | 9 | 9 | 7 |
|  |  | 0.5 | 8 | 7 | 9 | 8 | 7 | 2 | 1 | 1 | 2 | 0 | 5 | 5 | 8 | 3 |
|  |  | 0.25 | 7 | 9 | 7 | 0 | 9 | 6 | 2 | 1 | 5 | 1 | 9 | 9 | 9 | 7 |
|  |  | 0.13 | 5 | 8 | 8 | 9 | 8 | 2 | 1 | 0 | 5 | 3 | 9 | 9 | 9 | 3 |
| 3 | HC≡C—C(CH₃)₂—O—CH₂—O—(3-Cl-C₆H₄)—NH—CO—N(CH₃)₂ | 1.0 | 9 | 9 | 9 | 9 | 9 | 8 | 8 | 2 | 8 | 6 | 9 | 9 | 9 | 8 |
|  |  | 0.5 | 9 | 9 | 9 | 9 | 9 | 9 | 6 | 2 | 5 | 5 | 9 | 9 | 9 | 6 |
|  |  | 0.13 | 7 | 9 | 7 | 7 | 9 | 7 | 2 | 2 | 2 | 2 | 5 | 9 | 8 | 2 |
| 4 | HC≡C—CH₂—O—CH₂—O—(3-Cl-C₆H₄)—NH—CO—N(CH₃)₂ | 1.0 | 9 | 9 | 9 | 9 | 9 | 8 | 8 | 2 | 5 | 3 | 5 | 9 | 9 | 2 |
|  |  | 0.25 | 7 | 9 | 9 | 9 | 9 | 2 | 2 | 2 | 5 | 2 | 5 | 9 | 9 | 3 |
|  |  | 0.13 | 9 | 9 | 9 | 9 | 9 | 9 | 7 | 2 | 5 | 2 | 9 | 9 | 9 | 7 |
|  |  | 0.06 | 2 | 3 | 7 | 0 | 9 | 3 | 2 | 0 | 2 | 3 | 3 | 3 | 2 | 2 |
| 5 | HC≡C—CH(CH₃)—O—CH₂—O—(2-Cl-C₆H₄)—NH—CO—N(CH₃)₂ | 1.0 | 9 | 9 | 9 | 9 | 9 | 8 | 3 | 2 | 7 | 3 | 9 | 9 | 9 | 8 |
|  |  | 0.5 | 9 | 9 | 9 | 9 | 9 | 8 | 2 | 2 | 6 | 5 | 9 | 9 | 9 | 6 |
|  |  | 0.25 | 9 | 9 | 9 | 9 | 9 | 9 | 3 | 1 | 8 | 7 | 9 | 9 | 9 | 7 |
|  |  | 0.13 | 9 | 9 | 9 | 9 | 9 | 9 | 9 | 9 | 9 | 9 | 9 | 9 | 9 | 8 |
| 6 | HC≡C—C(CH₃)₂—O—CH₂—O—(C₆H₄)—NH—CO—N(CH₃)₂ | 1.0 | 7 | 9 | 9 | 9 | 9 | 3 | 3 | 0 | 2 | 0 | 5 | 9 | 9 | 2 |
|  |  | 0.25 | 9 | 9 | 9 | 0 | 9 | 8 | 3 | 2 | 5 | 5 | 5 | 9 | 9 | 7 |
|  |  | 0.13 | 9 | 9 | 9 | 9 | 9 | 8 | 9 | 2 | 8 | 7 | 9 | 9 | 9 | 8 |
|  |  | 0.06 | 9 | 9 | 9 | 9 | 9 | 5 | 9 | 9 | 9 | 9 | 9 | 9 | 9 | 8 |
| 7 | HC≡C—CH₂—O—CH₂—O—(3-NH—CO—N(OCH₃)CH₃)—C₆H₄ | 1.0 | 9 | 8 | 8 | 8 | 7 | 2 | 0 | 0 | 0 | 0 | 5 | 5 | 7 | 3 |
|  |  | 0.5 | 3 | 5 | 5 | 0 | 5 | 2 | 1 | 1 | 1 | 0 | 3 | 5 | 8 | 0 |
|  |  | 0.25 | 9 | 8 | 8 | 8 | 8 | 2 | 0 | 0 | 0 | 0 | 3 | 5 | 9 | 1 |
|  |  | 0.13 | 9 | 9 | 9 | 9 | 9 | 9 | 3 | 3 | 6 | 2 | 9 | 7 | 9 | 8 |
| 8 | HC≡C—CH(CH₃)—O—CH₂—O—(C₆H₄)—NH—CO—N(OCH₃)CH₃ | 1.0 | 9 | 9 | 9 | 9 | 9 | 9 | 2 | 0 | 0 | 0 | 0 | 3 | — | 0 |
|  |  | 0.5 | 8 | 8 | 9 | 8 | 9 | 9 | 1 | 1 | 1 | 1 | 2 | 3 | 8 | 2 |
|  |  | 0.25 | 9 | 9 | 9 | 9 | 9 | 9 | 2 | 2 | 3 | 3 | 9 | 3 | 9 | 3 |
|  |  | 0.13 | 2 | 3 | 3 | 9 | 1 | 1 | 0 | 0 | 0 | 0 | 0 | 3 | — | 0 |

TABLE II-continued

Postemergence Herbicidal Activity

| Compound of Example Number | Structure | Treatment lb./acre | Annual Weeds | | | | | | | | | | | | Crops | | | |
|---|---|---|---|---|---|---|---|---|---|---|---|---|---|---|---|---|---|---|
| | | | LA | MU | PI | RAG | MG | VE | BA | CR | GRF | WO | COR | COT | SOY | R |
| 9 | HC≡C−C(CH₃)(CH₃)−O−CH₂−⌬−NH−CO−N(OCH₃)(CH₃) | 1.0<br>0.5<br>0.25<br>0.13 | 9<br>9<br>3<br>3 | 9<br>8<br>3<br>1 | 9<br>9<br>3<br>2 | 9<br>0<br>0<br>0 | 9<br>8<br>0<br>0 | 9<br>5<br>1<br>1 | 9<br>7<br>1<br>1 | 9<br>8<br>1<br>1 | 9<br>9<br>1<br>1 | 9<br>7<br>3<br>2 | 9<br>6<br>3<br>1 | 9<br>6<br>2<br>1 | 7<br>2<br>2<br>2 | 3<br>1<br>1<br>0 |
| 10 | CH₂=CHCH₂−O−CH₂−⌬(Cl)−NH−CO−N(CH₃)₂ | 10.0 | 9 | 9 | 9 | 9 | 9 | 9 | 9 | 9 | 9 | 9 | 9 | — | — | — |
| 15 | HC≡C−C(CH₃)(CH₃)−O−CH₂−⌬(Cl)−NH−CO−N(OCH₃)(CH₃) | 1.0<br>0.25<br>0.13<br>0.02 | 9<br>9<br>9<br>3 | 9<br>9<br>9<br>1 | 9<br>9<br>9<br>2 | 9<br>5<br>2<br>0 | 9<br>9<br>6<br>1 | 7<br>6<br>5<br>0 | 7<br>5<br>1<br>0 | 9<br>7<br>2<br>0 | 9<br>3<br>2<br>1 | 6<br>6<br>1<br>0 | 6<br>3<br>3<br>1 | 9<br>9<br>9<br>1 | 9<br>8<br>5<br>1 | 5<br>3<br>3<br>0 |
| 16 | H₂C=C(CH₃)−CH₂−O−CH₂−⌬−NH−CO−N(CH₃)₂ | 2.0<br>1.0<br>0.5 | 9<br>9<br>3 | 9<br>9<br>5 | 9<br>9<br>2 | 9<br>5<br>0 | 9<br>9<br>3 | 7<br>5<br>0 | 7<br>3<br>0 | 9<br>8<br>3 | 9<br>8<br>3 | 9<br>6<br>2 | 9<br>6<br>2 | 9<br>6<br>1 | 9<br>5<br>1 | 5<br>3<br>1 |
| 19 | HC≡C−CH₂−O−CH₂−⌬−NH−CO−N(OCH₃)(CH₃) | 4.0<br>1.0<br>0.25 | 9<br>8<br>8 | 9<br>9<br>8 | 9<br>8<br>8 | 9<br>7<br>0 | 9<br>8<br>3 | 7<br>3<br>0 | 7<br>3<br>0 | 9<br>8<br>3 | 9<br>8<br>3 | 9<br>6<br>2 | 9<br>2<br>0 | 9<br>8<br>0 | 9<br>8<br>5 | 7<br>6<br>0 |
| 21 | HC≡C−CH₂−O−CH₂−⌬−NH−CO−NHCH₃ | 4.0<br>1.0<br>0.25<br>0.06 | 9<br>9<br>9<br>2 | 9<br>9<br>9<br>2 | 9<br>9<br>9<br>2 | 9<br>9<br>9<br>0 | 9<br>9<br>9<br>0 | 9<br>9<br>9<br>0 | 9<br>9<br>9<br>0 | 9<br>9<br>9<br>0 | 9<br>9<br>9<br>0 | 9<br>9<br>9<br>0 | 9<br>9<br>9<br>0 | 9<br>9<br>9<br>2 | 9<br>9<br>9<br>2 | 9<br>6<br>6<br>0 |
| 18 | HC≡C−C(CH₃)(CH₃)−O−CH₂−⌬−NH−CO−NHCH₃ | 1.0<br>0.25 | 9<br>9 | 9<br>9 | 9<br>9 | 9<br>7 | 9<br>9 | 9<br>1 | 7<br>1 | 9<br>1 | 9<br>1 | 9<br>8 | 9<br>2 | 9<br>2 | 9<br>7 | 9<br>2 |
| 20 | HC≡C−C(CH₃)(CH₃)−O−CH₂−⌬−NH−CO−N(OCH₃)(CH₃) | 4.0<br>1.0<br>0.25<br>0.06 | 9<br>9<br>9<br>8 | 9<br>9<br>9<br>8 | 9<br>9<br>9<br>9 | 9<br>9<br>9<br>1 | 9<br>9<br>9<br>7 | 9<br>9<br>9<br>4 | 9<br>9<br>9<br>7 | 9<br>9<br>9<br>8 | 9<br>9<br>9<br>3 | 9<br>9<br>9<br>7 | 9<br>9<br>9<br>3 | 9<br>9<br>9<br>7 | 9<br>9<br>9<br>5 | 9<br>9<br>9<br>1 |

TABLE II-continued

Postemergence Herbicidal Activity

| Compound of Example Number | Structure | Treatment lb./acre | Annual Weeds | | | | | | | | | | | Crops | | | |
|---|---|---|---|---|---|---|---|---|---|---|---|---|---|---|---|---|---|
| | | | LA | MU | PI | RAG | MG | VE | BA | CR | GRF | WO | COR | COT | SOY | R |
| 17 | HC≡C—C(CH₃)₂—O—CH₂—O—⌬—NH—CO—N(CH₃)₂ | 4.0<br>1.0<br>0.25<br>0.06 | 9<br>9<br>9<br>8 | 9<br>9<br>9<br>2 | 9<br>9<br>0<br>0 | 9<br>9<br>2<br>0 | 9<br>9<br>0<br>0 | 9<br>9<br>2<br>0 | 9<br>9<br>0<br>0 | 9<br>9<br>0<br>0 | 9<br>9<br>0<br>0 | 9<br>9<br>5<br>0 | 9<br>9<br>2<br>0 | 9<br>9<br>5<br>0 | 9<br>9<br>5<br>0 | 9<br>9<br>2<br>0 |
| 14 | HC≡C—CH₂—O—CH₂—O—⌬—NH—CO—N—OCH₃<br>CH₃ | 1.0<br>0.25<br>0.13<br>0.06 | 9<br>9<br>9<br>8 | 9<br>9<br>9<br>2 | 9<br>9<br>9<br>0 | 9<br>9<br>9<br>3 | 9<br>9<br>9<br>2 | 9<br>9<br>9<br>0 | 9<br>9<br>9<br>2 | 9<br>9<br>9<br>1 | 9<br>9<br>9<br>5 | 9<br>9<br>9<br>5 | 9<br>9<br>9<br>5 | 9<br>9<br>9<br>6 | 9<br>9<br>9<br>5 | 9<br>9<br>9<br>3 |
| 22 | HC≡C—CH₂—C(CH₃)₂—O—CH—O—⌬—NH—CO—N(CH₃)₂<br>CH₃ | 0.5<br>0.25<br>0.13<br>0.06 | 9<br>9<br>9<br>7 | 9<br>9<br>9<br>7 | 9<br>9<br>7<br>0 | 9<br>9<br>9<br>0 | 7<br>6<br>6<br>0 | 9<br>9<br>2<br>0 | 9<br>9<br>7<br>0 | 9<br>9<br>8<br>0 | 9<br>9<br>7<br>0 | 9<br>9<br>9<br>0 | 5<br>7<br>5<br>0 | 9<br>9<br>6<br>0 | 9<br>9<br>5<br>0 | 9<br>9<br>2<br>0 |
| 23 | HC≡C—CH₂—O—CH—O—⌬—NH—CO—N(CH₃)₂<br>CH₃ | 1.0<br>0.5<br>0.25<br>0.13 | 9<br>9<br>9<br>2 | 9<br>9<br>9<br>6 | 9<br>8<br>3<br>0 | 9<br>9<br>6<br>3 | 9<br>9<br>9<br>0 | 9<br>6<br>5<br>0 | 9<br>9<br>3<br>0 | 9<br>9<br>3<br>0 | 9<br>9<br>3<br>0 | 9<br>9<br>3<br>0 | 9<br>9<br>6<br>0 | 9<br>9<br>8<br>0 | 9<br>9<br>6<br>0 | 9<br>9<br>5<br>0 |
| 25 | HC≡C—CH₂—O—CH—O—⌬(Cl)—NH—CO—N(CH₃)₂<br>CH₃ | 0.50<br>0.25<br>0.13<br>0.06 | 9<br>9<br>9<br>9 | 9<br>9<br>9<br>9 | 9<br>9<br>9<br>7 | 9<br>9<br>9<br>7 | 9<br>9<br>9<br>5 | 9<br>9<br>6<br>0 | 9<br>9<br>8<br>2 | 9<br>9<br>8<br>3 | 9<br>9<br>9<br>7 | 9<br>9<br>9<br>6 | 9<br>9<br>7<br>5 | 9<br>9<br>9<br>8 | 9<br>9<br>7<br>5 | 9<br>9<br>9<br>2 |
| 27 | HC≡C—CH₂—O—CH₂—O—⌬(Cl)—NH—CO—NH—C₂H₅ | 4.0<br>1.0<br>0.5 | 8<br>7<br>3 | 8<br>7<br>0 | 9<br>7<br>0 | 9<br>7<br>0 | 7<br>5<br>0 | 0<br>0<br>0 | 7<br>7<br>2 | 9<br>8<br>7 | 9<br>9<br>5 | 9<br>6<br>0 | —<br>—<br>— | 9<br>8<br>7 | 9<br>9<br>5 | 9<br>8<br>6 |
| 28 | HC≡C—CH₂—O—CH₂—O—⌬(Cl)—NH—CO—NH—C₃H₇-n | 10.0 | 9 | 6 | 6 | 6 | 0 | 0 | 0 | 0 | 0 | 0 | — | — | — | — |

TABLE II-continued

Postemergence Herbicidal Activity

| Compound of Example Number | Structure | Treatment lb./acre | Annual Weeds | | | | | | | | | | | Crops | | | |
|---|---|---|---|---|---|---|---|---|---|---|---|---|---|---|---|---|---|
| | | | LA | MU | PI | RAG | MG | VE | BA | CR | GRF | WO | COR | COT | SOY | R |
| 29 | HC≡C—CH₂—O—⟨Cl⟩—NH—CO—NH—CH(CH₃)₂ | 10.0 | 8 | 7 | 8 | 5 | 2 | 0 | 0 | 0 | 0 | 0 | — | — | — | — |
| 30 | HC≡C—CH₂—O—⟨Cl⟩—NH—CO—NH—C₄H₉-n | 4.0<br>1.0<br>0.5 | 9<br>8<br>5 | 8<br>6<br>1 | 9<br>9<br>6 | 9<br>5<br>0 | 1<br>0<br>0 | 0<br>0<br>0 | 5<br>0<br>0 | 2<br>0<br>0 | 6<br>0<br>0 | 1<br>0<br>0 | — — —<br>— — —<br>— — — | 3<br>2<br>1 | 3<br>2<br>— | 0<br>0<br>0 |
| 31 | HC≡C—CH—O—CH₂—⟨Cl⟩—NH—CO—NHCH₃<br>CH₃ | 1.0<br>0.25<br>0.06 | 9<br>9<br>9 | 9<br>9<br>9 | 9<br>9<br>8 | 9<br>7<br>3 | 9<br>3<br>0 | 9<br>3<br>0 | 9<br>2<br>0 | 9<br>2<br>1 | 9<br>6<br>2 | 0<br>0<br>0 | — — —<br>— — —<br>— — — | 7<br>5<br>1 | 2<br>2<br>— | 5<br>3<br>0 |
| 32 | HC≡C—CH₂—O—CH₂—⟨Cl⟩—NH—CO—NHC₄H₉-n | 0.50<br>0.25<br>0.13<br>0.06 | 9<br>9<br>9<br>9 | 9<br>9<br>9<br>9 | 9<br>9<br>8<br>9 | 9<br>3<br>3<br>7 | 9<br>8<br>3<br>0 | 9<br>8<br>3<br>0 | 9<br>7<br>2<br>0 | 9<br>7<br>8<br>0 | 9<br>8<br>8<br>0 | 3<br>0<br>0<br>0 | 6<br>1<br>—<br>— | 9<br>9<br>9<br>9 | 7<br>8<br>9<br>9 | 7<br>3<br>2<br>0 |

EXAMPLE 48

The selective preemergence herbicidal acitivity of the compounds of the invention is exemplified by the following tests in which the seeds of a variety of monocotyledonous and dicotyledonous plants are separately mixed with potting soil and a one half inch layer is placed on top of approximately 1½ inch of soil in separate two-inch square plastic pots. After planting, the pots are sprayed with the selected aqueous acetone solution containing test compound in sufficient quantity to provide the equivalent of about 0.13 to 4 pounds per acre of test compound per pot. The treated pots are then placed on greenhouse benches and cared for in accordance with greenhouse procedures. Three weeks after treatment, the tests are terminated and each pot is examined and rated according to the rating system set forth in the preceding example. The tabulated results of these tests establish the selective herbicidal proficiency of the test compounds, when properly applied, for controlling a variety of undesirable plant species. The data also indicate broad spectrum activity of the compounds when applied at relatively high rates. Results are reported in the Table below.

TABLE III
Preemergence Herbicidal Activity

| Compound of Example Number | Structure | Treatment lb./acre | LA | MU | PI | RAG | MG | VE | BA | CR | GRF | WO | COR | COT | SOY | R |
|---|---|---|---|---|---|---|---|---|---|---|---|---|---|---|---|---|
| 6 | O—CH$_2$—O—CH$_2$—C≡CH with NHCON(CH$_3$)$_2$ (phenyl) | 4.0 / 1.0 / 0.5 / 0.25 | 9/9/9/2 | 9/8/2 | 9/9/9/3 | 9/9/6/0 | 9/9/9 | 9/9/9 | 9/9/9 | 9/9/9 | 9/9/9 | 9/8/6 | 9/7/0 | 9/0/0 | 9/0/0 | 9/8/2/0 |
| 2 | HC≡C—CH$_2$—O—CH$_2$—O—(phenyl)—NH—CO—N(CH$_3$)$_2$ | 4.0 / 1.0 / 0.25 / 0.13 | 9/9/9 | 9/9/9 | 9/9/9 | 9/9/9/3 | 9/9/5/0 | 9/9/8/0 | 9/9/7/0 | 9/9/8/1 | 9/9/8/0 | 9/8/1/0 | 9/7/1 | 9/7/0 | 9/3/0 | 9/9/7/1 |
| 3 | HC≡C—C(CH$_3$)$_2$—O—CH$_2$—O—(phenyl)—NH—CO—N(CH$_3$)$_2$ | 4.0 / 1.0 / 0.25 / 0.13 | 9/9/9/2 | 9/9/9/2 | 9/9/9/3 | 9/9/7/0 | 9/9/7/2 | 9/9/9/3 | 9/9/8/0 | 9/9/8/1 | 9/9/8/2 | 9/7/1/0 | 9/7/1/0 | 9/9/2 | 9/9/3 | 9/9/8 |
| 4 | HC≡C—CH$_2$—O—CH$_2$—O—(Cl-phenyl)—NH—CO—N(CH$_3$)$_2$ | 4.0 / 1.0 / 0.25 / 0.13 | 9/9/0 | 9/9/0 | 9/9/9/0 | 9/9/6/0 | 9/7/0 | 9/9/3/0 | 9/9/2 | 9/9/1 | 9/9/2 | 9/9/1 | 9/9/1 | 9/9/0 | 9/9/0 | 9/9/0 |
| 5 | HC≡C—CH$_2$—O—CH$_2$—O—(Cl-phenyl)—NH—CO—N(CH$_3$)$_2$ | 4.0 / 1.0 / 0.25 / 0.13 | 9/9/5 | 9/9/7 | 9/9/9/5 | 9/9/9/5 | 9/9/8 | 9/9/6 | 9/9/5 | 9/9/7/3 | 9/9/5/3 | 9/7/1/1 | 9/7/1/0 | 9/7/0 | 9/9/0 | 9/9/6 |
| 1 | HC≡C—C(CH$_3$)$_2$—O—CH$_2$—O—(Cl-phenyl)—NH—CO—N(CH$_3$)$_2$ | 4.0 / 1.0 / 0.25 / 0.13 | 9/9/9/5 | 9/9/9/7 | 9/9/9 | 9/9/9/0 | 9/9/7/2 | 9/9/6/2 | 9/9/3/2 | 9/9/1/0 | 9/9/5/2 | 9/9/6/0 | 9/9/1/0 | 9/9/0/0 | 9/9/3/0 | 9/9/6/0 |
| 7 | HC≡C—CH$_2$—O—CH$_2$—O—(phenyl)—NH—CO—N(OCH$_3$)(CH$_3$) | 4.0 / 1.0 / 0.5 / 0.25 | 9/9/9 | 9/9/9 | 9/9/9 | 9/9/5 | 9/5/1 | 9/2 | 9/2/3 | 9/3/1 | 9/5/2 | 9/6/5/1 | 9/2/1/0 | 9/3/0 | 9/3/0 | 9/9/3/0 |
| 8 | HC≡C—CH(CH$_3$)—O—CH$_2$—O—(phenyl)—NH—CO—N(OCH$_3$)(CH$_3$) | 4.0 / 1.0 / 0.5 / 0.25 | 9/8/5 | 9/9/5 | 9/9/5 | 9/9/5 | 9/7/0 | 9/8/2 | 9/8/6 | 9/8/6 | 9/7/0 | 7/5/1 | 8/2/0 | 9/8/0 | 9/7/0 | 9/9/3 |

TABLE III-continued
Preemergence Herbicidal Activity

| Compound of Example Number | Structure | Treatment lb./acre | Annual Weeds |  |  |  |  |  |  |  |  |  |  | Crops |  |  |  |
|---|---|---|---|---|---|---|---|---|---|---|---|---|---|---|---|---|---|
| | | | LA | MU | PI | RAG | MG | VE | BA | CR | GRF | WO | COR | COT | SOY | R |
| 9 | HC≡C—C(CH₃)₂—O—CH₂—O—C₆H₄—NH—CO—N(OCH₃)(CH₃) | 4.0 / 1.0 / 0.5 / 0.25 | 9 9 9 8 | 9 9 9 0 | 9 9 9 7 | 0 0 0 0 | 0 0 0 3 | 9 9 2 0 | 9 8 7 2 | 8 7 0 0 | 9 5 1 0 | 7 2 1 0 | 0 1 2 0 | 9 0 0 0 | 9 5 0 0 | 9 7 1 0 |
| 10 | CH₂=CHCH₂—O—CH₂—O—C₆H₄—NH—CO—N(OCH₃)(CH₃) | 1.0 / 0.5 | 9 8 | 9 0 | 8 2 | 2 0 | 1 3 | 0 8 | 7 3 | 6 0 | 1 0 | 3 0 | 3 0 | 2 0 | 9 5 | 9 8 |
| 11 | CH₂=CHCH₂—O—CH₂—O—C₆H₄—NH—CO—N(OCH₃)₂ | 1.0 / 0.5 | 9 9 | 9 0 | 9 8 | 0 2 | 0 2 | 0 2 | 9 3 | 6 6 | 0 1 | 3 6 | 0 2 | 0 2 | 9 5 | 9 2 |
| 12 | HC≡C—CH₂—O—CH₂—O—(Cl)C₆H₃—NH—CO—N(OCH₃)(CH₃) | 4.0 / 1.0 / 0.5 | 9 9 8 | 9 9 0 | 9 9 9 | 9 9 0 | 9 7 3 | 9 9 0 | 9 9 3 | 9 9 0 | 9 9 0 | 2 0 0 | 9 4 0 | 5 — — | 9 9 2 | 9 9 0 |
| 13 | HC≡C—C(CH₃)₂—O—CH₂—O—(Cl)C₆H₃—NH—CO—NH—CH₃ | 4.0 / 1.0 / 0.5 / 0.25 | 9 9 9 3 | 9 9 9 9 | 9 9 9 9 | 9 9 3 0 | 9 3 2 0 | 9 9 0 0 | 9 9 7 3 | 9 9 0 0 | 9 9 7 0 | 9 9 2 0 | 9 9 7 0 | 9 9 5 0 | 9 9 6 0 | 9 9 8 0 |
| 14 | HC≡C—C(CH₃)₂—O—CH₂—O—(Cl)C₆H₃—NH—CO—N(OCH₃)(CH₃) | 4.0 / 1.0 / 0.25 / 0.13 | 9 9 9 8 | 9 9 9 3 | 9 9 9 9 | 0 3 3 0 | 2 6 9 2 | 9 9 9 0 | 9 9 8 0 | 9 2 2 0 | 9 8 8 0 | 0 0 8 0 | 0 0 2 0 | 0 0 3 0 | 0 1 9 0 | 0 0 2 6 |
| 15 | HC≡C—C(CH₃)₂—O—CH₂—O—(Cl)C₆H₃—NH—CO—N(OCH₃)(CH₃) | 4.0 / 1.0 / 0.25 / 0.13 | 9 8 1 1 | 9 9 9 9 | 9 9 9 5 | 0 0 9 5 | 0 0 1 9 | 0 2 9 3 | 0 5 6 7 | 0 7 8 — | 0 3 7 — | 0 0 1 1 | 0 1 1 2 | 0 — 2 9 | 0 0 9 — | 0 0 2 6 |
| 16 | H₂C=C(CH₃)—CH₂—O—CH₂—O—C₆H₄—NH—CO—N(CH₃)₂ | 2.0 / 1.0 / 0.5 / 0.25 | 0 7 8 0 | 9 9 9 0 | 5 8 9 0 | 0 0 5 0 | 0 0 1 9 | 0 2 3 9 | 0 5 6 7 | 0 1 8 — | 0 1 3 — | 0 0 1 1 | 0 1 1 2 | 0 — 2 9 | 0 0 9 — | 0 3 2 3 |

TABLE III-continued
Preemergence Herbicidal Activity

| Compound of Example Number | Structure | Treatment lb./acre | LA | MU | PI | RAG | Annual Weeds MG | VE | BA | CR | GRF | WO | COR | Crops COT | SOY | R |
|---|---|---|---|---|---|---|---|---|---|---|---|---|---|---|---|---|
| 19 | HC≡C—CH₂—O—CH₂—⟨C₆H₄⟩—NH—CO—NHCH₃ | 4.0 / 1.0 / 0.25 | 9/8/3 | 9/9/1 | 9/9/0 | 9/9/0 | 9/0/0 | 9/0/0 | 9/0/0 | 9/5/0 | 9/3/0 | 9/3/0 | 9/5/0 | 9/3/0 | 9/8/0 | 9/7/0 |
| 21 | HC≡C—CH₂—O—CH₂—⟨C₆H₄⟩—NH—CO—N(CH₃)(OCH₃) | 4.0 / 1.0 / 0.25 | 9/9/8 | 9/9/9 | 9/9/8 | 9/8/0 | 9/1/0 | 9/1/0 | 9/3/0 | 9/5/2 | 9/3/0 | 9/3/0 | 9/0/0 | 9/3/0 | 9/6/1 | 9/6/0 |
| 20 | HC≡C—C(CH₃)₂—O—CH₂—⟨C₆H₄⟩—NH—CO—N(CH₃)(OCH₃) | 4.0 / 1.0 / 0.25 | 9/8/2 | 9/9/1 | 9/8/0 | 9/2/0 | 9/0/0 | 9/0/0 | 9/2/0 | 9/2/0 | 9/2/0 | 9/5/0 | 9/7/0 | 9/2/0 | 9/8/2 | 9/6/0 |
| 18 | HC≡C—C(CH₃)₂—O—CH₂—⟨C₆H₄⟩—NH—CO—NH—CH₃ | 1.0 / 0.25 / 0.06 | 9/9/1 | 9/9/0 | 9/8/0 | 9/7/0 | 9/5/0 | 9/8/0 | 9/8/0 | 9/8/1 | 9/8/1 | 9/9/0 | 9/7/0 | 9/3/0 | 9/8/5 | 9/6/0 |
| 17 | HC≡C—C(CH₃)₂—O—CH₂—⟨C₆H₄⟩—NH—CO—N(CH₃)₂ | 4.0 / 1.0 / 0.25 | 9/7/1 | 9/9/3 | 9/9/0 | 9/5/0 | 9/5/0 | 9/5/0 | 9/5/2 | 9/6/0 | 9/6/0 | 9/0/0 | 9/0/0 | 9/0/0 | 9/1/0 | 9/0/0 |
| 23 | HC≡C—CH(CH₃)—O—⟨C₆H₄⟩—NH—CO—N(CH₃)₂ | 4.0 / 1.0 | 9/9 | 9/9 | 9/9 | 9/3 | 9/7 | 9/8 | 9/5 | 9/8/7 | 9/6 | 9/7 | 9/0 | 9/0 | 9/3 | 9/0 |
| 25 | HC≡C—CH₂—O—CH(CH₃)—⟨C₆H₄⟩—NH—CO—N(CH₃)₂ | 1.0 / 0.5 / 0.25 | 8/7/5 | 8/7/3 | 7/5/0 | 7/5/0 | 9/5/1 | 9/5/0 | 8/0/0 | 9/0/0 | 8/0/0 | 7/0/0 | 0/—/0 | 0/—/0 | 7/2/0 | 0/0/0 |
| 26 | HC≡C—CH₂—O—CH(CH₃)—⟨C₆H₃Cl⟩—NH—CO—N(CH₃)₂ | 1.0 / 0.5 / 0.25 / 0.13 | 9/9/9/3 | 9/9/8/1 | 9/9/7/2 | 9/9/7/0 | 9/9/2/0 | 9/8/3/0 | 9/8/2/0 | 9/8/3/0 | 9/5/0/0 | 9/6/0/0 | 9/2/0/0 | 0/0/0/— | 9/0/0/— | 7/3/1/0 |
| 27 | HC≡C—CH₂—O—CH₂—⟨C₆H₃Cl⟩—NH—CO—NH—C₂H₅ | 4.0 / 1.0 | 9/9 | 9/9 | 9/9 | 7/7 | 0/0 | 0/1 | 0/0 | 0/7 | 0/5 | 0/0 | 0/0 | 0/7 | 0/5 | 0/0 |

TABLE III-continued

Preemergence Herbicidal Activity

| Compound of Example Number | Structure | Treatment lb./acre | Annual Weeds | | | | | | | | | | Crops | | | |
|---|---|---|---|---|---|---|---|---|---|---|---|---|---|---|---|---|
| | | | LA | MU | PI | RAG | MG | VE | BA | CR | GRF | WO | COR | COT | SOY | R |
| 29 | HC≡C—CH₂—O—⟨Cl⟩—NH—CO—NH—CH(CH₃)₂ | 4.0<br>1.0 | 9<br>8 | 8<br>2 | 8<br>2 | 4<br>9 | 4<br>0 | 0<br>0 | 1<br>0 | 3<br>0 | 1<br>0 | 0<br>0 | 0<br>0 | 7<br>0 | 5<br>0 | 0<br>0 |
| 30 | HC≡C—CH₂—O—⟨Cl⟩—NH—CO—NH—C₄H₉-n | 4.0<br>1.0 | 8<br>7 | 9<br>2 | 3<br>5 | 7<br>8 | 0<br>0 | 0<br>0 | 2<br>0 | 2<br>0 | 0<br>0 | 0<br>0 | 0<br>0 | 2<br>0 | 2<br>0 | 0 |
| 31 | HC≡C—CH—O—CH₂—⟨Cl⟩—NH—CO—NHCH₃<br>   CH₃ | 2.0<br>1.0<br>0.5 | 9<br>9<br>9 | 9<br>9<br>9 | 9<br>9<br>9 | 9<br>9<br>7 | 9<br>5<br>2 | 9<br>9<br>9 | 7<br>6<br>5 | 9<br>8<br>5 | 7<br>6<br>2 | 2<br>1<br>0 | 5<br>0<br>0 | 3<br>0<br>0 | 6<br>1<br>0 | 7<br>5<br>0 |
| 32 | HC≡C—CH₂—O—CH₂—⟨Cl⟩—NH—CO—NH—C₄H₉-n | 4.0<br>1.0 | 9<br>7 | 9<br>9 | 0<br>0 | 0<br>0 | 1<br>0 | 7<br>0 | 0<br>3 | 0<br>0 | 0<br>0 | 0<br>0 | 0<br>0 | 0<br>0 | 0<br>0 | 0<br>0 |

I claim:

1. 1-Methoxy-1-methyl-3-{p-[(1,1-dimethyl-2-propynyloxy)-methoxy]phenyl} urea.

* * * * *